(12) United States Patent
Fujimori

(10) Patent No.: US 7,998,059 B2
(45) Date of Patent: Aug. 16, 2011

(54) ENDOSCOPIC IMAGING APPARATUS AND CAPSULE-TYPE ENDOSCOPE

(75) Inventor: Noriyuki Fujimori, Nagano (JP)

(73) Assignee: Olympus Corporation, Tokyo (JP)

( * ) Notice: Subject to any disclaimer, the term of this patent is extended or adjusted under 35 U.S.C. 154(b) by 1311 days.

(21) Appl. No.: 11/486,950

(22) Filed: Jul. 14, 2006

(65) Prior Publication Data

US 2006/0264703 A1 Nov. 23, 2006

Related U.S. Application Data

(63) Continuation of application No. PCT/JP2005/000546, filed on Jan. 18, 2005.

(30) Foreign Application Priority Data

| Jan. 19, 2004 | (JP) | 2004-010712 |
| Jan. 22, 2004 | (JP) | 2004-014620 |
| Jan. 26, 2004 | (JP) | 2001-017138 |

(51) Int. Cl.
*A61B 1/04* (2006.01)

(52) U.S. Cl. ............... 600/109; 600/176; 348/340

(58) Field of Classification Search ............ 600/109, 600/176; 348/76, 340
See application file for complete search history.

(56) References Cited

U.S. PATENT DOCUMENTS

| 4,879,991 | A |   | 11/1989 | Ogiu |
| 5,228,430 | A | * | 7/1993 | Sakamoto ............ 600/134 |
| 6,796,939 | B1 |   | 9/2004 | Hirata et al. |
| 6,855,111 | B2 |   | 2/2005 | Yokoi et al. |
| 6,918,872 | B2 |   | 7/2005 | Yokoi et al. |
| 7,229,407 | B2 |   | 6/2007 | Suzushima |
| 7,465,271 | B2 |   | 12/2008 | Kanazawa |
| 7,473,218 | B2 |   | 1/2009 | Segawa et al. |
| 7,505,802 | B2 |   | 3/2009 | Yoshino |
| 7,511,733 | B2 |   | 3/2009 | Takizawa et al. |
| 7,837,614 | B2 |   | 11/2010 | Segawa et al. |
| 7,892,164 | B2 |   | 2/2011 | Segawa et al. |
| 2001/0007051 | A1 |   | 7/2001 | Nakashima et al. |
| 2001/0012073 | A1 | * | 8/2001 | Toyoda et al. ............ 348/335 |
| 2002/0140836 | A1 | * | 10/2002 | Miyake et al. ............ 348/340 |
| 2002/0145676 | A1 | * | 10/2002 | Kuno et al. ............ 348/340 |
| 2003/0137595 | A1 | * | 7/2003 | Takachi ............ 348/340 |

(Continued)

FOREIGN PATENT DOCUMENTS

EP 1 329 189 A2 7/2003

(Continued)

OTHER PUBLICATIONS

U.S. Office Action dated Jan. 13, 2011 received in related U.S. Appl. No. 11/872,623.

(Continued)

*Primary Examiner* — John P Leubecker
(74) *Attorney, Agent, or Firm* — Scully, Scott, Murphy & Presser, P.C.

(57) ABSTRACT

An endoscopic imaging includes an image sensor having a polygonal outline; a lens for focusing an image onto the image sensor; a lens support member abutting on the image sensor, and supporting the lens; and an abutting portion formed while extending from a lower edge portion of the lens support member, the abutting portion abutting on at least two sides of an outline of the image sensor to position the lens support member so that the lens is positioned at a predetermined position of the image sensor.

7 Claims, 18 Drawing Sheets

U.S. PATENT DOCUMENTS

| | | |
|---|---|---|
| 2003/0171649 A1* | 9/2003 | Yokoi et al. .................. 600/109 |
| 2004/0027459 A1 | 2/2004 | Segawa et al. |
| 2004/0171914 A1 | 9/2004 | Avni |
| 2004/0225189 A1 | 11/2004 | Kimoto et al. |
| 2004/0225190 A1 | 11/2004 | Kimoto et al. |
| 2005/0018068 A1* | 1/2005 | Tsai et al. .................... 348/335 |
| 2005/0043586 A1 | 2/2005 | Suzushima |
| 2005/0046735 A1* | 3/2005 | Tan et al. .................... 348/340 |
| 2005/0049461 A1 | 3/2005 | Honda et al. |
| 2005/0049462 A1 | 3/2005 | Kanazawa |
| 2005/0054902 A1 | 3/2005 | Konno |
| 2005/0099531 A1* | 5/2005 | Wu et al. ..................... 348/374 |
| 2005/0179805 A1* | 8/2005 | Avron et al. ................. 348/340 |
| 2005/0195323 A1* | 9/2005 | Graham ....................... 348/374 |
| 2005/0212947 A1* | 9/2005 | Sato et al. ................... 348/340 |
| 2005/0237419 A1* | 10/2005 | Van Gemert ................ 348/340 |
| 2005/0288557 A1* | 12/2005 | Yokoi et al. .................. 600/176 |
| 2006/0229592 A1 | 10/2006 | Yokoi et al. |
| 2007/0055105 A1* | 3/2007 | Matsuzawa et al. .......... 600/176 |
| 2007/0142708 A1 | 6/2007 | Yokoi et al. |
| 2007/0173696 A1 | 7/2007 | Fujimori et al. |
| 2008/0146877 A1 | 6/2008 | Matsuzawa et al. |
| 2008/0167528 A1 | 7/2008 | Segawa et al. |

FOREIGN PATENT DOCUMENTS

| | | |
|---|---|---|
| EP | 1 618 834 A1 | 1/2006 |
| EP | 1 618 835 A1 | 1/2006 |
| EP | 1 707 102 A1 | 10/2006 |
| JP | 6-70882 A | 3/1994 |
| JP | 2000-258698 | 9/2000 |
| JP | 2001-091860 | 4/2001 |
| JP | 2001-231744 | 8/2001 |
| JP | 2004-065772 | 3/2004 |
| WO | WO 2004/096028 A1 | 11/2004 |
| WO | WO 2004/096029 A1 | 11/2004 |
| WO | WO 2005/067782 A1 | 7/2005 |

OTHER PUBLICATIONS

U.S. Office Action dated Mar. 29, 2011 corresponding to related U.S. Appl. No. 11/872,638.

Supplementary Partial European Search Report dated Nov. 16, 2010.

* cited by examiner

US 7,998,059 B2

ENDOSCOPIC IMAGING APPARATUS AND CAPSULE-TYPE ENDOSCOPE

CROSS-REFERENCE TO RELATED APPLICATIONS

This application is a continuation of PCT international application Ser. No. PCT/JP2005/000546 filed Jan. 18, 2005 which designates the United States, incorporated herein by reference, and which claims the benefit of priority from Japanese Patent Applications No. 2004-010712, filed Jan. 19, 2004; No. 2004-014620, filed Jan. 22, 2004; and No. 2004-017138, filed Jan. 26, 2004, all incorporated herein by reference.

BACKGROUND OF THE INVENTION

1. Field of the Invention

The present invention relates to an endoscopic imaging apparatus and a capsule endoscope which obtain an image inside a subject when the capsule endoscope is putted in the subject.

2. Description of the Related Art

Recently, instead of the conventional endoscope, a swallowing type endoscope, i.e., a so-called capsule endoscope receives attention because pain of a subject can be reduced and so on. For example, as shown in FIG. 21, in the capsule endoscope, a wiring board 2 and a power source 3 are accommodated in a sealed container 1 formed in a capsule shape. A functional circuit is formed on the wiring board. The capsule endoscope is configured to obtain the image inside the subject as being the test body while the capsule endoscope is putted in a body cavity of the subject. The sealed container 1 includes a cylindrical container main body 1a having a bottom and a front cover 1b molded by an optical material. The sealed container 1 is configured to attach the front cover 1b to a front portion of the container main body 1a while water-tightness is secured between the container main body 1a and the front cover 1b, after the wiring board 2 and the power source 3 are accommodated in the container main body 1a. The sealed container 1 is formed in a size to an extent in which a human can swallow the sealed container 1, and both end portions of the sealed container 1 are formed in a hemispherical shape. In order to form a circuit of the above-described functions circuit, various functional components and electronic components such as an illumination unit 4, a lens unit 5, an imaging device 6, and a wireless transmission unit 7 are mounted on the wiring board 2.

In the case of use of the capsule endoscope, the subject can swallow the capsule endoscope while a power source 3 is turned on. When the capsule endoscope is putted inside the body cavity of the subject, while an observation range of the subject such as the stomach, the small intestine, and the large intestine is illuminated with illumination light emitted from illumination unit 4 through the front cover 1b until the capsule endoscope is discharged to the outside of the body, reflected light incident through the front cover 1b is focused to an imaging device 6 through a lens unit 5, and the reflected light focused to the imaging device 6 is output as an image signal. Then, the image signal output from the imaging device 6 is wirelessly transmitted to the outside by a wireless transmission unit 7, and image information on the subject can be received and observed by a receiver placed outside the subject (For example, see JP-A No. 2001-91860 (KOKAI)).

However, in the capsule endoscope, it is necessary that the components be correctly positioned among each other in order to obtain a good image within the subject. Particularly, in an optical system that focuses the reflected light incident through the front cover 1b on the imaging device 6, it is necessary to correctly perform the positioning, because the optical system has a direct influence on image quality in the subject.

Therefore, in assembling the capsule endoscope, it is necessary that the correct positioning be simultaneously performed, which makes assembling work remarkably complicated and thus taking a considerable time to assemble the capsule endoscope.

SUMMARY OF THE INVENTION

An endoscopic imaging apparatus according to one aspect of the present invention includes an image sensor having a polygonal outline; a lens for focusing an image onto the image sensor; a lens support member abutting on the image sensor, and supporting the lens; and an abutting portion formed while extending from a lower edge portion of the lens support member, the abutting portion abutting on at least two sides of an outline of the image sensor to position the lens support member so that the lens is positioned at a predetermined position of the image sensor.

A capsule endoscope according to another aspect of the present invention includes an illumination board section in which an illumination unit for emitting illumination light illuminating a tested region of a subject is arranged; an imaging board section in which an image sensor imaging the tested region of the subject is arranged; a flexible wiring board section which is connected to the illumination board section and the imaging board section, the flexible wiring board section being made from a flexible material in which the illumination board section and the imaging board section are integrally formed; a lens support member which supports a lens for focusing reflected light of the illumination light from the tested region and has a cylindrical member whose one end side is positioned with respect to the image sensor; a hole which is made while piercing through the illumination board section, has an inner diameter larger than an outer diameter of the lens support member in order to fit the lens support member in the hole; and a supporting unit which positions and supports the illumination board section with respect to the lens support member when the flexible wiring board section is folded to insert other end side of the lens support member into the hole, the supporting unit being provided in the lens support member.

A capsule endoscope according to still another aspect of the present invention is configured to obtain an image inside a subject when the capsule endoscope is putted in the subject. The capsule endoscope includes a sealed container which accommodates a functional circuit; a front cover which is made of an optical material, is formed in a hemispherical and dome shape whose proximal end is opened, and forms a front portion of the sealed container; an internal member which is arranged in the front cover at the proximal end; a lens unit which is held by the internal member and focuses light incident through the front cover; and a positioning unit which is formed between the front cover and the internal member and alternately aligns a center of entrance pupil of the front cover with a center of entrance pupil of the lens unit on a same optical axis by engaging the internal member with the front cover when the internal member is inserted into the proximal end of the front cover.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of an endoscopic imaging apparatus and a capsule endoscope according to the invention will be described in detail with reference to the accompanying drawings. However, the present invention is not limited to the embodiments.

Figure 1:
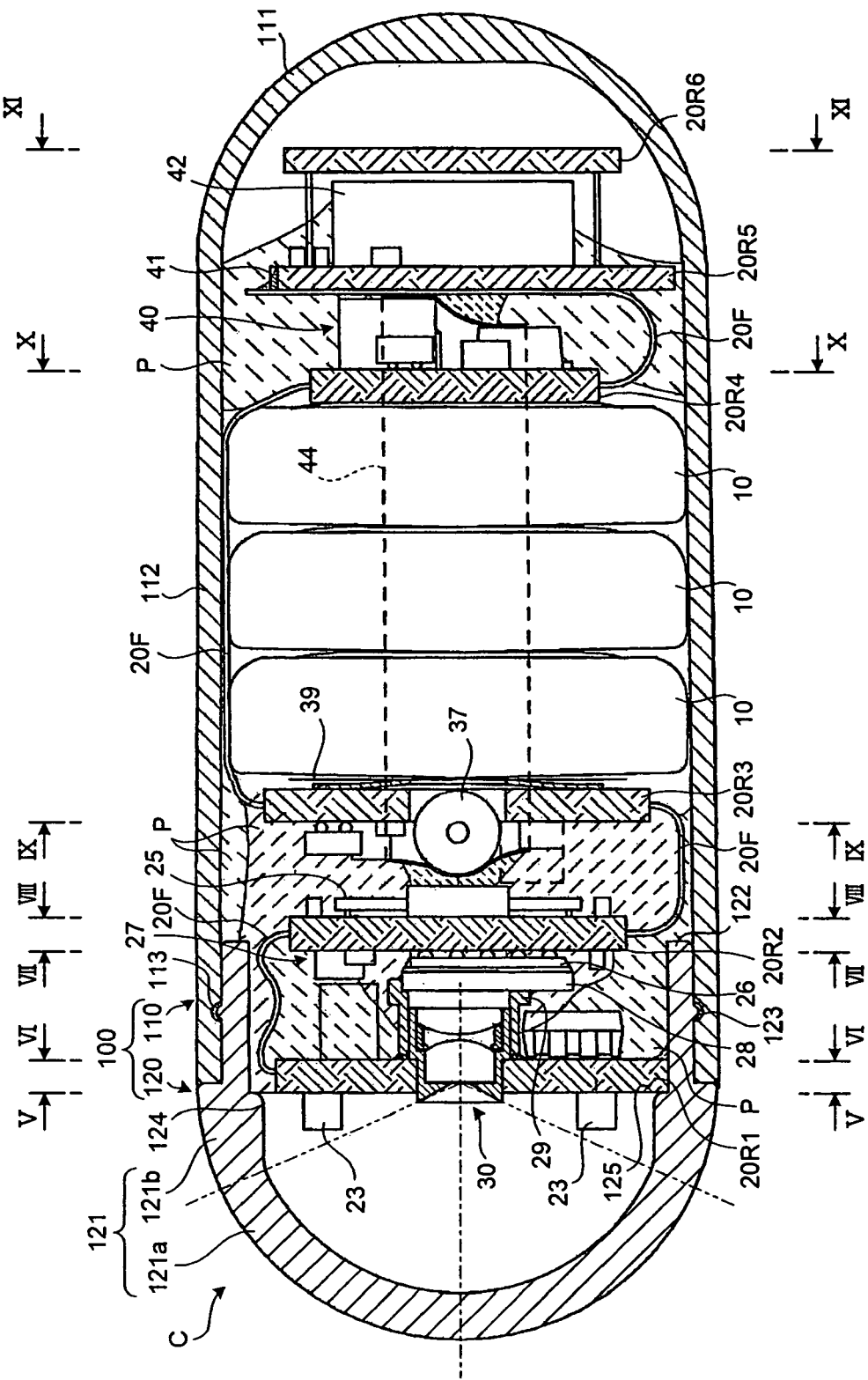
FIG. 1 is a sectional side view showing a capsule endoscope according to an embodiment of the present invention.

FIG. 1 is a sectional side view showing a capsule endoscope according to an embodiment of the invention. A capsule endoscope C illustrated in FIG. 1 has a size which can be putted from a mouth of a subject such as human or animal into its body. The capsule endoscope C obtains image data which is of internal information on alimentary canals such as the gaster, the small intestine, and the large intestine, after the capsule endoscope C is put into the body until the capsule endoscope C is discharged from the body. The capsule endoscope C includes an internal power source 10, a rigid-flexible wiring board 20 provided with a functional circuit which executes predetermined functions, and a capsule-shaped sealed container 100 accommodating the internal power source 10 and the wiring board 20.

The internal power source 10 accumulates drive power supplied to the functional circuit. In the embodiment, three general-purpose silver oxide button cells (hereinafter also simply referred to as button cell 10) are used as the internal power source 10. The three button cells 10 are not always required, but the number of button cells 10 may appropriately be determined according to a time during which the functional circuit is operated. The silver oxide cell is not always used. Alternatively a rechargeable battery, a self-generating battery, and the like may be used.

The wiring board 20 is a complex board (hereinafter sometimes referred to as rigid-flexible wiring board 20 as appropriate) which includes plural rigid wiring board sections 20R and a flexible wiring board section 20F sequentially connecting the plural rigid wiring board section 20R. The rigid wiring board section 20R is made from a relatively rigid base material such as glass epoxy resin. Various functional components and electronic components constituting the functional circuit are mainly mounted on the rigid wiring board section 20R. The flexible wiring board section 20F is made from a flexible film base material such as polyimide resin and polyester resin and serves as mainly a cable which electrically connects the plural rigid wiring board sections 20R to each other.

The functional circuit formed on the wiring board 20 has plural predetermined functional sections necessary to obtain image data, for example, an illumination function for illuminating a predetermined imaging range with illumination light, an imaging function for converting the reflected light by the irradiation of the illumination light into the image signal, a switch function for turning on and off supply voltage from the internal power source 10, a voltage conversion function for adjusting an internal power source voltage to a predetermined constant voltage, a transmission processing function for modulating and amplifying a given image signal, an antenna function for externally outputting the modulated and amplified image signal in the form of the wireless signal, and a control function for controlling the whole of the functions.

In the embodiment, the functional sections are divided into plural pieces of the rigid wiring board section 20R. Specifically, the rigid wiring board section 20R of the wiring board 20 includes an illumination board section 20R1 for implementing the illumination function, an imaging board section 20R2 for implementing the imaging function and the control function, a switch board section 20R3 for implementing the switch function, a power source board section 20R4 for implementing the voltage conversion function, a transmission board section 20R5 for implementing the transmission processing function, and an antenna board section 20R6 for implementing the antenna function.

As shown in FIGS. 1 to 6, the illumination board section 20R1 is disk-shaped and has an attachment hole 21 in the center thereof and a straight-line portion 22R1 in a part of a circumferential surface thereof. The attachment hole 21 and the straight-line portion 22R1 are references of the electronic components arranged on the illumination board section 20R1. The attachment hole 21 is small round, and a lens unit 30 described later is attached in the attachment hole 21. The straight-line portion 22R1 is formed by linearly cutting a circumferential portion of the illumination board section 20R1 and is provided at a right angle to an extending direction of the flexible wiring board section 20F.

Figure 4:
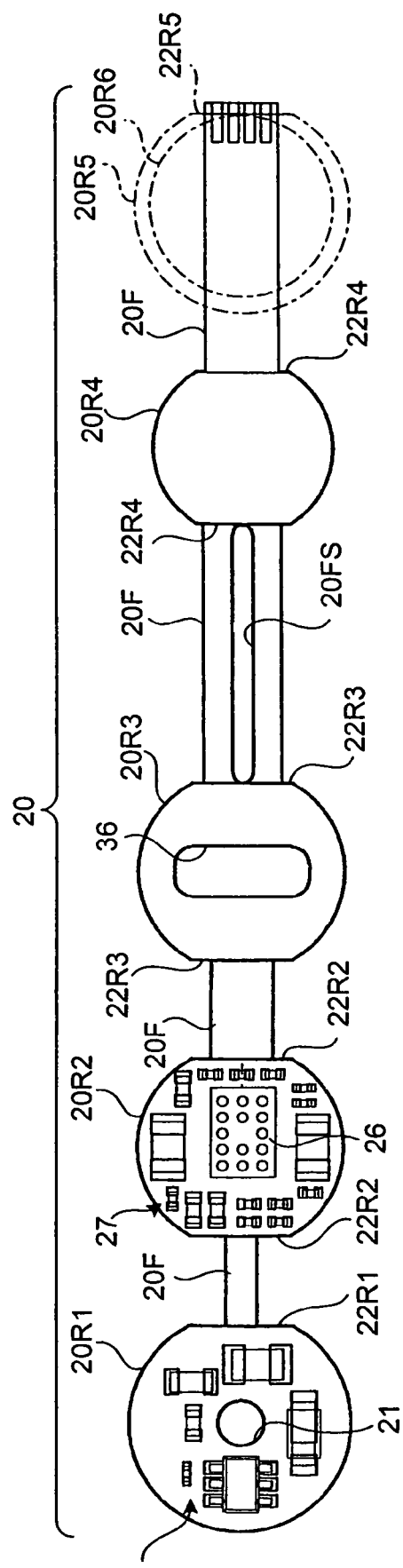
FIG. 4 is a bottom view of FIG. 2.
Figure 5:
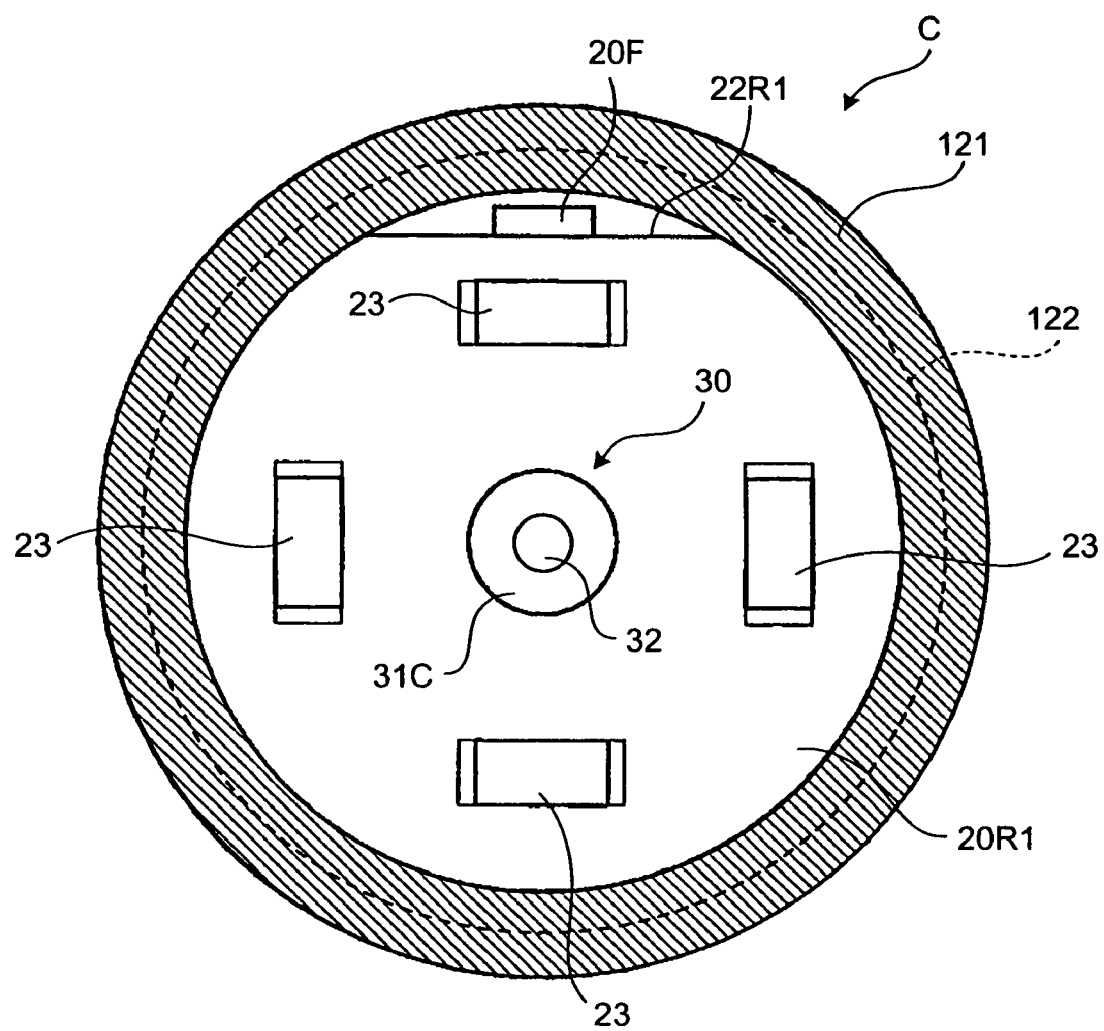
FIG. 5 is a cross-sectional view taken along line V-V of FIG. 1.

A light-emitting device 23 such as a white light diode (Light Emitting Diode) is mounted on one of mounting surfaces of the illumination board section 20R1 in order to implement the illumination function. As shown in FIGS. 4 and 5, the four light-emitting devices 23 are mounted at equal intervals around the attachment hole 21 while equally separated away from the attachment hole 21. The four light-emitting devices 23 are not always required, but any number of, for example three or less or five or more of, light-emitting devices 23 may be adopted as long as the light-emitting devices 23 sufficiently exert the illumination function. The diode is not always used as the light-emitting device. Alternatively, EL (electroluminescence) may be used.

On the other hand, the electronic components constituting a drive circuit 24 for the light-emitting device 23 are mounted on the other mounting surface of the illumination board section 20R1. The electronic components include tall electronic components such as a driving electronic component for driving the light-emitting device 23 and an electronic component for stably supplying voltage to the light-emitting device 23 and low-profile electronic components such as a small capacitor and a small resistor.

In the case where the illumination board section 20R1 and the imaging board section 20R2 are laminated with a desired interval by folding the flexible wiring board section 20F connecting the illumination board section 20R1 and the imaging board section 20R2, the tall electronic components such as the driving electronic component and the electronic component for stably supplying the voltage face the low-profile electronic components such as the small capacitor and the small resistor which are arranged in a surface (front surface of imaging board section 20R2) oppositely facing the illumination board section 20R1 of the imaging board section 20R2.

On the other hand, in the case where the illumination board section 20R1 and the imaging board section 20R2 are laminated by folding the flexible wiring board section 20F connecting the illumination board section 20R1 and the imaging board section 20R2, the low-profile electronic components such as the small capacitor and the small resistor face a later-mentioned tall and large capacitor which is arranged in the surface (front surface of imaging board section 20R2) oppositely facing the illumination board section 20R1 of the imaging board section 20R2.

That is, in the rigid-flexible wiring board 20 in which the illumination board section 20R1 and the imaging board section 20R2 are arranged by folding the flexible wiring board section 20F connecting the illumination board section 20R1 and the imaging board section 20R2, while the tall and large capacitor arranged in the front surface of the imaging board section 20R2, the low-profile small capacitor, and the electronic components such as the capacitor are alternately combined, the tall driving electronic component, the electronic component for stably supplying the voltage, the low-profile electronic components such as the small capacitor and the small resistor are arranged in the back surface of the illumination board section 20R1.

Therefore, a distance between the illumination board section 20R1 and the imaging board section 20R2 can be narrower than a sum of a height of the tall electronic component arranged in the back surface of the illumination board section 20R1 and the tall electronic component arranged in the front surface of the imaging board section 20R2. The flexible wiring board section 20F is formed to be longer than an assembled length of a later-mentioned image sensor and the lens unit 30.

After the illumination board section 20R1 having the above configuration is arranged while oppositely facing the imaging board section 20R2 at a predetermined interval, the illumination board section 20R1 and the imaging board section 20R2 are fixed to each other while electrically insulated by a adhesive agent having an insulating property.

As shown in FIGS. 1 to 4, 7, and 8, the imaging board section 20R2 is disk-shaped, has a diameter equal to or slightly smaller than that of the illumination board section 20R1, and has two straight-line portions 22R2 in the circumferential surface. The straight-line portions 22R2 are formed by linearly cutting the circumferential portion of the imaging board section 20R2. The straight-line portions 22R2 are parallel to each other, and are provided at a right angle to the extending direction of the flexible wiring board section 20F. The straight-line portions 22R2, i.e., the extending direction of the flexible wiring board section 20F becomes a reference of the electronic components arranged on the imaging board section 20R2.

An image sensor provided as a ball grid array package is mounted on one mounted surface (front surface) of the imaging board section 20R2 such that the extending direction of the flexible wiring board section 20F coincides with a direction of pixel array. In the image sensor, a pixel surface of a rectangular solid-state imaging device such as CCD (Charge Coupled Diode) or CMOS (Complementary Metal Oxide Semiconductor) is coated with a cover glass 28. An outline of the cover glass 28 is formed in a polygonal shape. (Hereinafter, the solid-state imaging device is simply referred to as CCD 26.)

As shown in FIGS. 1 and 12 to 16, a holder 29 (lens support member) is attached to the cover glass 28, and a lens unit 30 is placed in the holder 29.

The holder 29 includes a cylindrical portion 29a which has a diameter larger than that of the pixel surface of the CCD 26, and a base 29b which is integrally formed with a proximal end portion of the cylindrical portion 29a. A hole portion made in the cylindrical portion 29a pierces through the base 29b to guide the light incident from the holder 29 onto the CCD 26. A lower surface of the base 29b, i.e., the outline of the surface abutting on an upper surface of the CCD 26 has a substantially square shape whose side is substantially equal to a short side of the cover glass 28. Abutting portions 29c extend downward from the two adjacent sides of the lower edge portion and abut on the side surfaces of the cover glass 28.

Figure 13:
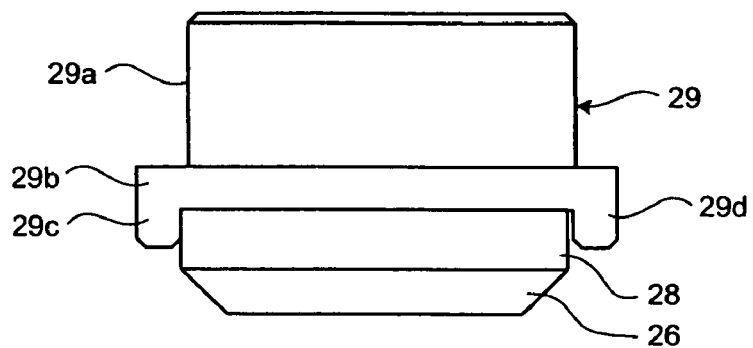
FIG. 13 is a front view showing CCD and a positioned holder.
Figure 14:
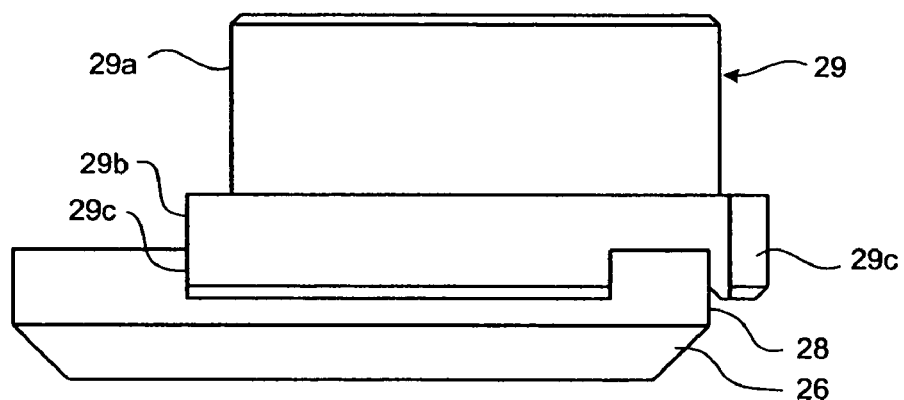
FIG. 14 is a side view showing CCD and the positioned holder.
Figure 15:
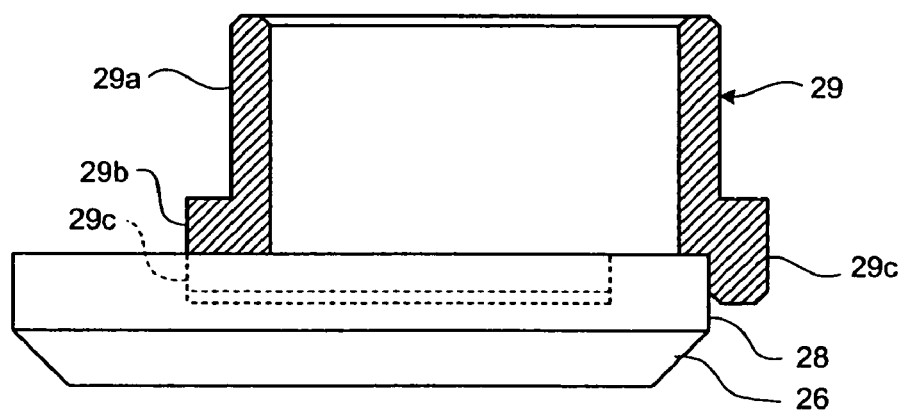
FIG. 15 is a sectional side view showing CCD and the positioned holder.

As shown in FIGS. 13 to 15, in the holder 29, while the lower surface of the base 29b abuts on the upper surface of the cover glass 28, the base 29b abuts on the side surfaces which are of the two adjacent sides of the upper surface of the cover glass 28. Therefore, the holder 29 is accurately attached to the cover glass 28 through the base 29b while an axial center of the cylindrical portion 29a is aligned with the central axis (optical axis) L of a visual field in the CCD 26.

Figure 12:
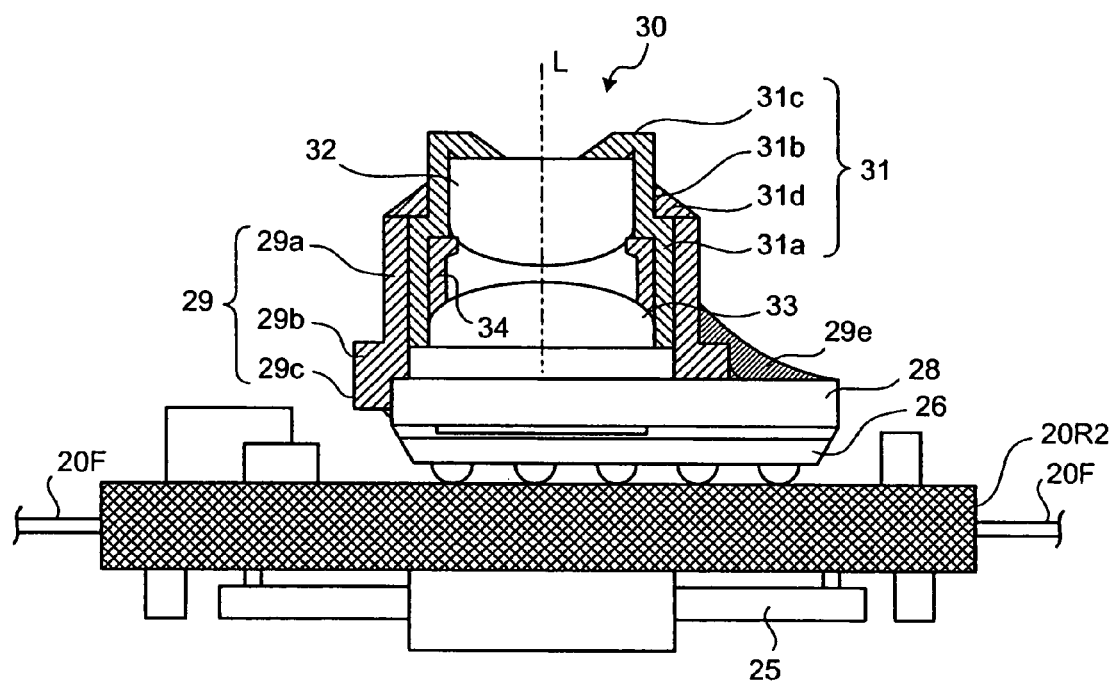
FIG. 12 is an enlarged cross-sectional view of the imaging board section of FIG. 1.

A reinforcement portion 29d having substantially the same shape as the abutting portion 29c extends from the lower edge portion of the holder 29, and the cover glass 28 and the holder 29 are fixed to each other by a black-colored adhesive agent after the attachment. As shown in FIG. 12, since a black-colored adhesive agent 29e is applied to an exposed surface where the cover glass 28 is not covered with the holder 29, the incidence of the light from the exposed surface can be prevented to project the clear image onto CCD 26.

The lens unit 30 includes a cylindrical lens frame 31 and a pair of lens members 32 and 33. A cylindrical slide portion 31a that has a relatively large outer diameter fitted in the cylindrical portion 29a of the holder 29, a cylindrical attachment portion 31b that is continuously provided to a front portion of the slide portion 31a while coaxially aligned with the slide portion 31a and has a relatively small diameter fitted in the attachment hole 21 of the illumination board section 20R1, and a light-shielding portion 31c which is projected inward from all the circumferences of the front portion of the attachment portion 31b are integrally formed in the lens frame 31. An outer circumferential surface of the lens frame 31 has a step portion 31d between the slide portion 31a and the attachment portion 31b. The front portion of the lens frame 31 is one which takes in the incident light focusing the image onto the CCD 26, and the light-shielding portion 31c is one which corresponds to an entrance pupil for defining an observation range of the image data with respect to the lens unit 30. An outer end surface of the light-shielding portion 31c is recessed in a funnel shape while tapered toward the central axis. A small-diameter portion and a large-diameter portion are formed in an inner circumferential surface of the lens frame 31, and a boundary portion between the small-diameter portion and the large-diameter portion are defined by a step portion. A small-diameter lens 32 is fitted in the small-diameter portion. In the small-diameter lens 32 having a large refractive index, the upper surface is formed flat, and the lower surface is formed in a convex surface. A flat surface portion of the small-diameter lens 32 abuts on the light-shielding portion 31c, and the circumferential surface portion of the small-diameter lens 32 is fitted in the small-diameter portion. A cylindrical spacer 34, and a large-diameter lens 33 which has a small refractive index and has a convex upper surface and a flat rear surface are fitted in the large-diameter portion. The spacer 34 separates the small-diameter lens 32 from the large-diameter lens 33 at a predetermined interval, and attaches the small-diameter lens 32 and the large-diameter lens 33 to the inside of the lens frame 31 while optical axes of the small-diameter lens 32 and the large-diameter lens 33 are aligned with each other. The lens unit 30 is slidably arranged in the cylindrical portion 29a of the holder 29 through the slide portion 31a while the light-shielding portion 31c is orientated outward, so that focus can be adjusted by appropriately changing a position in an optical axis direction with respect to the pixel surface of the CCD 26.

Electronic components constituting a drive circuit 27 for the CCD 26 are mounted on one surface of the imaging board section 20R2. Specifically, large capacitors for a power source voltage circuit for driving the CCD 26 are arranged next to the CCD 26 based on the arrangement of the CCD 26; small electronic components such as capacitors and resistors necessary to drive the CCD 26 are orderly arranged away from the CCD 26 and the large capacitors.

On the other hand, in the other surface (back surface) of the imaging board section 20R2, a processor device (hereinafter simply referred to as DSP 25) such as a DSP (Digital Signal Processor) for implementing the control function is mounted by flip chip bonding, and the electronic components such as capacitors are orderly arranged based on the arrangement of the DSP 25. This arrangement allows the electronic components to be integrated, contributing to the downsizing of the capsule endoscope. The DSP 25 performs not only the control function but also the drive control of CCD signal processing and illumination board section.

Figure 8:
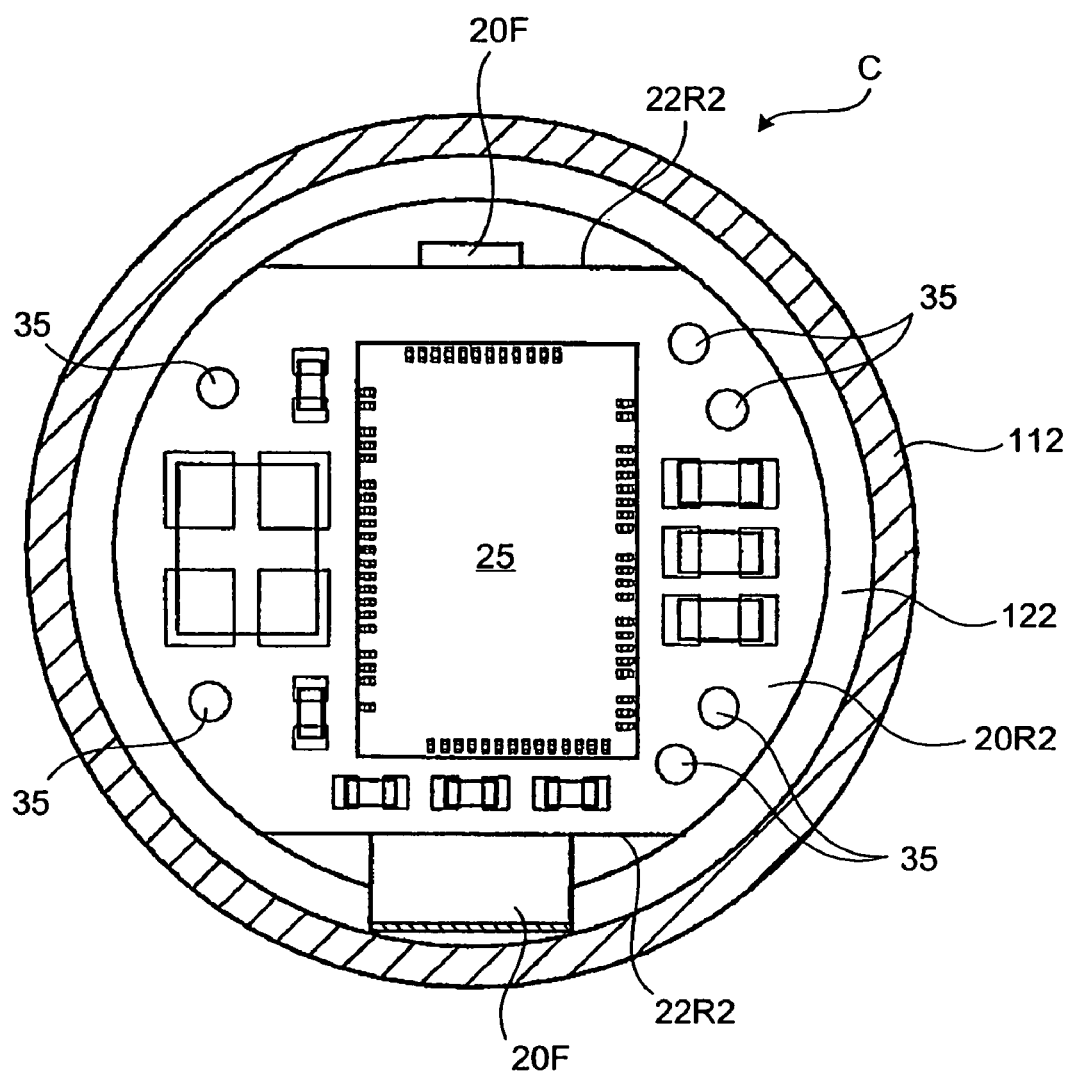
FIG. 8 is a cross-sectional view taken along line VIII-VIII of FIG. 1.
Figure 9:
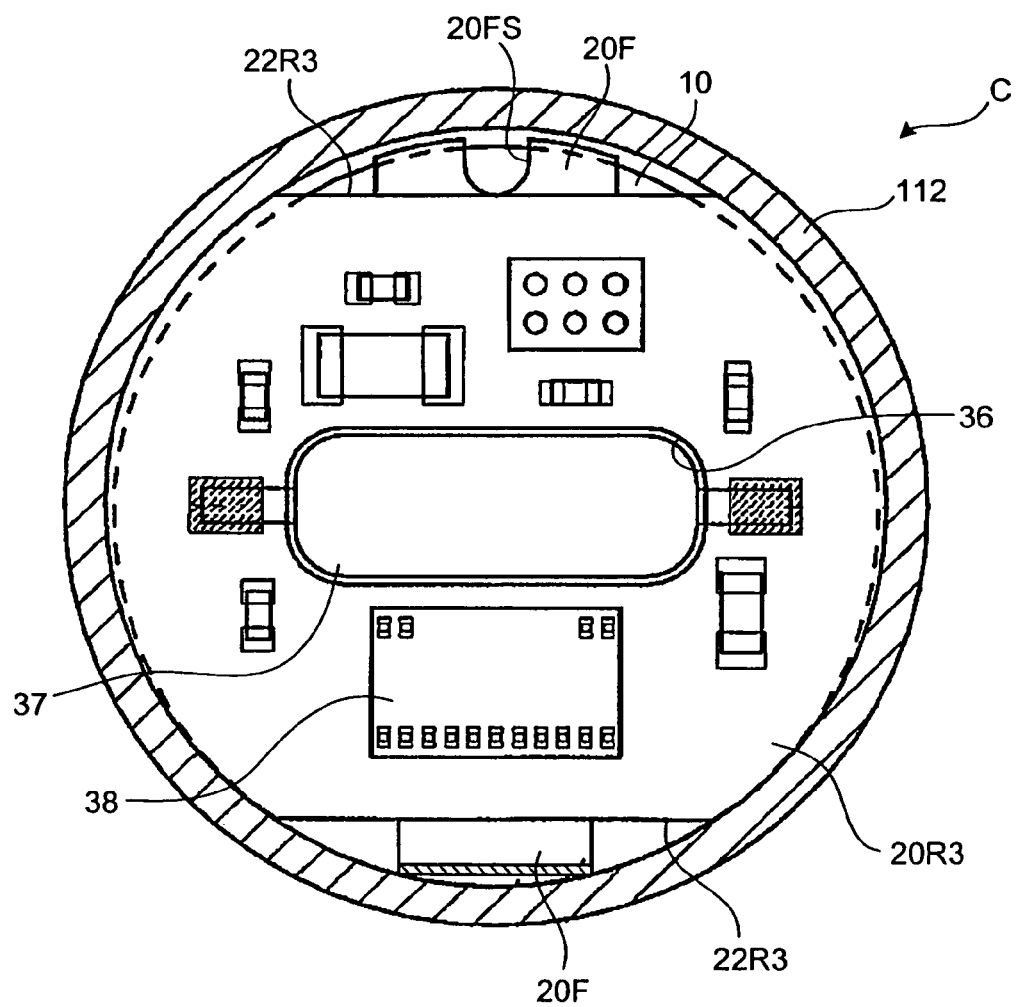
FIG. 9 is a cross-sectional view taken along line IX-IX of FIG. 1.
Figure 10:
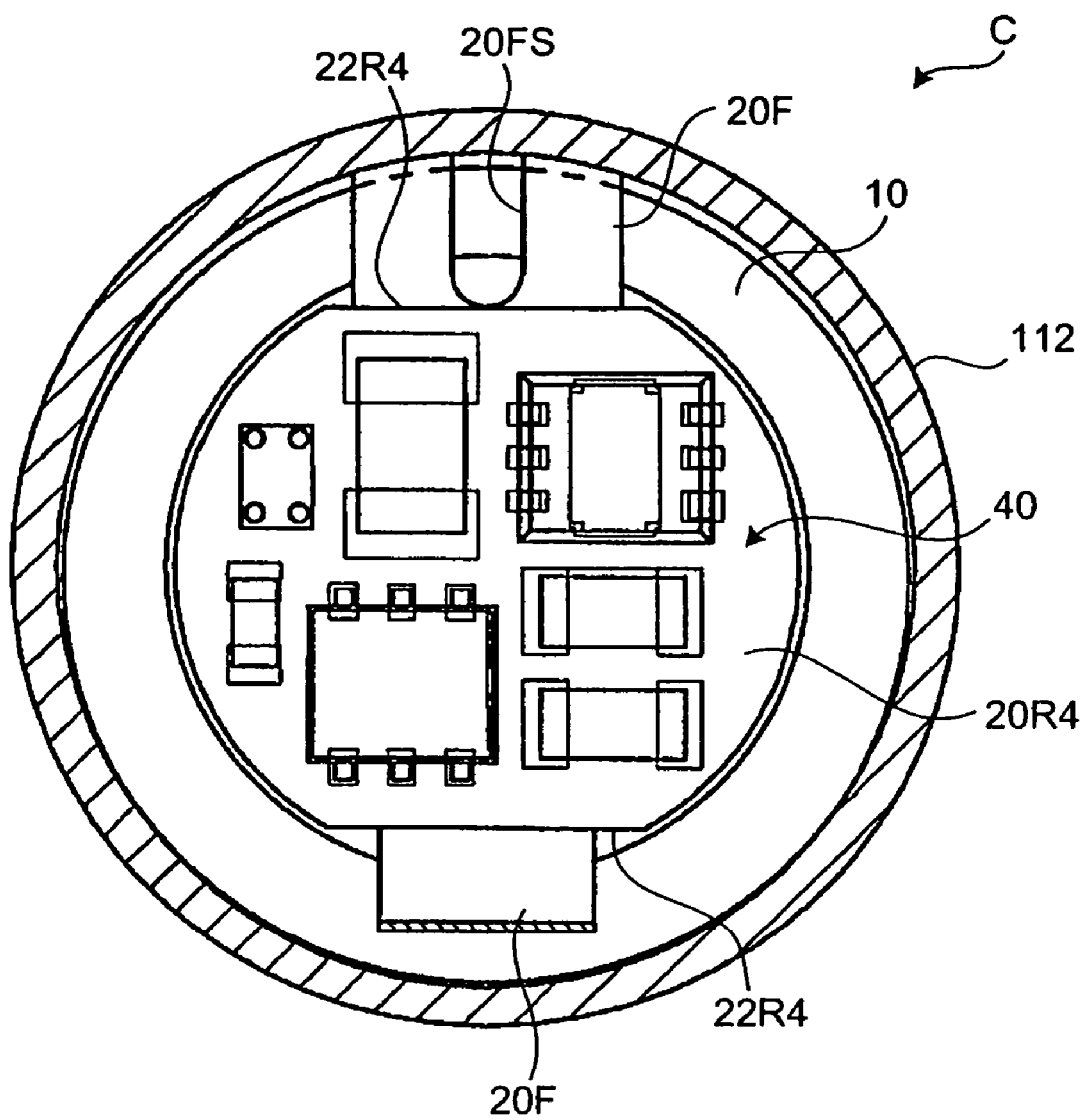
FIG. 10 is a cross-sectional view taken along line X-X of FIG. 1.

As shown in FIG. 8, in the imaging board section 20R2, plural pad portions 35 which is of external terminals are provided in a region which is located out of the mounting areas of the electronic components in the other mounting surface. The pad portion 35 is an electrically conductive portion which is roundly exposed in the mounting surface of the imaging board section 20R2. The pad portion 35 includes a portion which functions as an external power supply terminal for directly supplying the electric power from an external power source (not shown) to the functional circuit and a portion which functions as an external input terminal for inputting an initial setting value of the functional circuit to a memory described later.

As shown in FIGS. 1 to 4 and 9, the switch board section 20R3 is disk-shaped and has a diameter equal to or slightly smaller than that of the imaging board section 20R2. Similarly to the imaging board section 20R2, the switch board section 20R3 has straight-line portions 22R3 at two points in the circumferential surface and has a relief hole 36 in a central portion thereof. The straight-line portions 22R3 are formed by linearly cutting the circumferential portion of the switch board section 20R3 and are provided in parallel with each other and at a right angle to the extending direction of the flexible wiring board section 20F. The straight-line portions 22R3, i.e., the extending direction of the flexible wiring board section 20F becomes a reference of the electronic components arranged on the switch board section 20R3. The relief hole 36 is used for accommodating a part of a later-mentioned reed switch 37 and is formed in a long hole shape extending along the straight-line portion 22R3.

The reed switch 37 for implementing the switch function is mounted in the switch board section 20R3 while a part of the reed switch 37 is accommodated in the relief hole 36 from one mounting surface side. Therefore, a projection height of the reed switch 37 can be suppressed on the front surface side. In one of mounting surfaces, the electronic components such as a memory 38, an oscillator, and a MIX are orderly arranged in the region around the relief hole 36.

The reed switch 37, responding to a magnetic field, is a latch-type switch which turns on and off the electric supply power from the internal power source 10. In the embodiment, the electric power supply from the internal power source 10 is turned off in the case where the magnetic field acts on the reed switch 37 by bringing a permanent magnet close to the reed switch 37; the electric power supply from the internal power source 10 is continuously turned on in the case where the magnetic field does not act on the reed switch 37.

The memory 38 is a volatile storage unit in which data such as the initial setting value of the DSP 25 necessary to drive the functional circuit is stored. Examples of the initial setting value of the DSP 25 include a white balance coefficient of the CCD 26, data for correcting failure caused by a variation in the CCD 26, and pixel defect address data of the CCD 26. The oscillator supplies a basic clock to the DSP 25. The MIX is mounted by flip chip bonding and has a function for mixing the two signals into one signal when two signals of an image signal output from the DSP 25 and a clock signal are transmitted. As shown in FIG. 1, a positive electrode contact member 39, which is a contact to a positive electrode of the button cell 10, formed in a disk spring is provided in the other mounting surface of the switch board section 20R3.

As shown in FIGS. 1 to 4 and 10, the power source board section 20R4 has a diameter smaller than that of the switch board section 20R3 as well as of a negative electrode of the button cell 10 is disk-shaped. Similarly to the switch board section 20R3, the power source board section 20R4 has a diameter smaller than that of the straight-line portions 22R4 at two points in the circumferential surface. The straight-line portions 22R4 are formed by linearly cutting the circumferential portion of the power source board section 20R4 and are provided in parallel with each other and at a right angle to the extending direction of the flexible wiring board section 20F. The straight-line portions 22R4, i.e., the extending direction of the flexible wiring board section 20F becomes a reference of the electronic components arranged on the power source board section 20R4.

In one of mounting surfaces of the power source board section 20R4, for example, the plural electronic components are mounted to form a DC-DC converter 40 in order to implement the voltage conversion function. The DC-DC converter 40 controls the voltage supplied from the battery in order to obtain the constant voltage necessary for the capsule endoscope. A negative electrode contact member (not shown), which is a contact to the negative electrode of the button cell 10, is provided in the other mounting surface of the power source board section 20R4.

As shown in FIGS. 1, 2, 4, and 11, the transmission board section 20R5 is disk-shaped and has a diameter equal to or slightly smaller than that of the switch board section 20R3. The transmission board section 20R5 is produced independently of the rigid-flexible wiring board 20, and one of mounting surfaces (front surface) of the transmission board section 20R5 and the flexible wiring board section 20F are connected by a through-hole land 41. Similarly to the illumination board section 20R1, the transmission board section 20R5 has a straight-line portion 22R5 in a part of the circumferential surface. The straight-line portion 22R5 is formed by linearly cutting the circumferential portion of the transmission board section 20R5. The straight-line portion 22R5 becomes a reference of the electronic components arranged on the transmission board section 20R5.

In the other mounting surface of the transmission board section 20R5, for example, the plural electronic components are mounted to form an RF (Radio Frequency) unit 42 in order to realize the transmission processing function.

Figure 11:
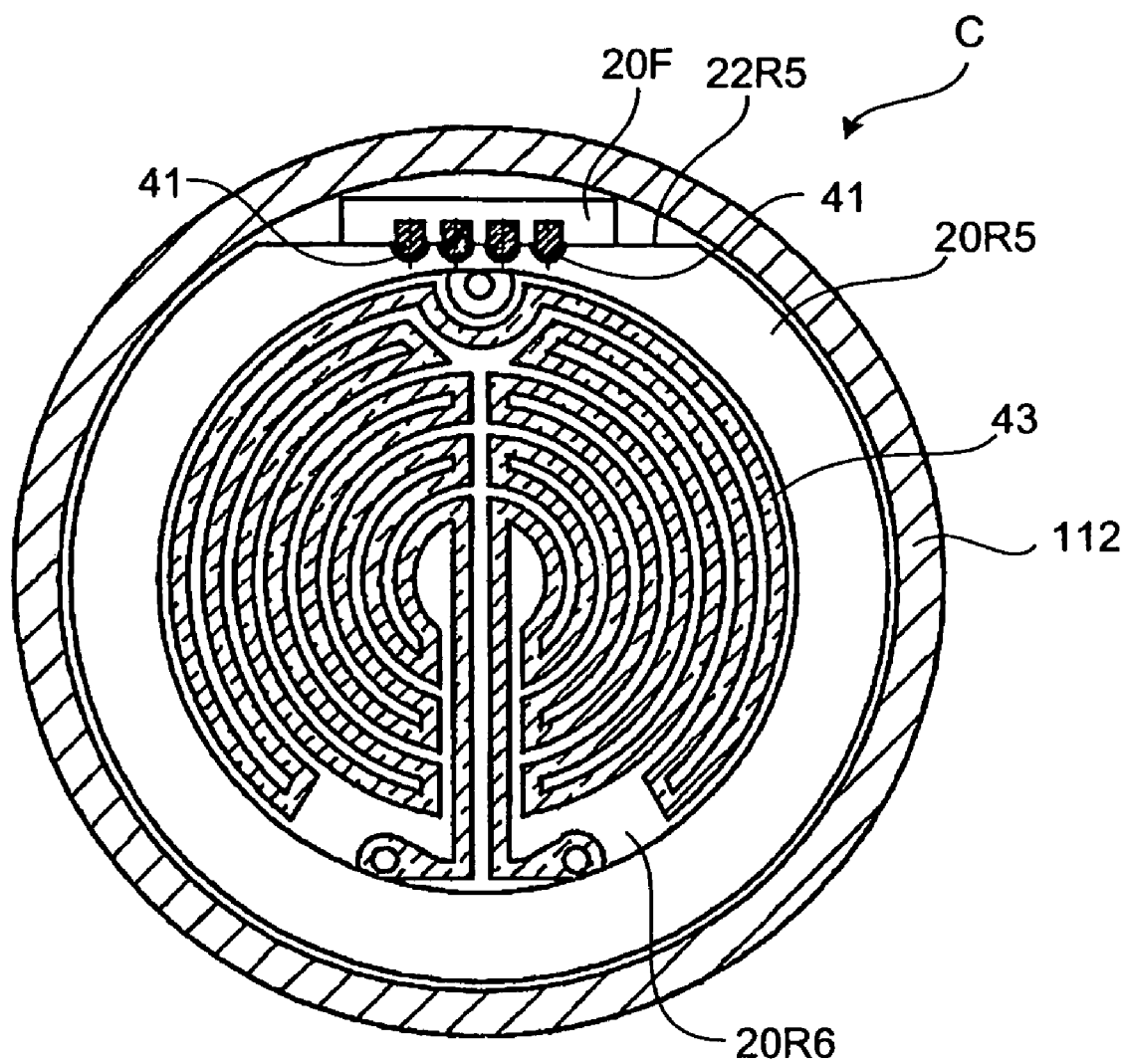
FIG. 11 is a cross-sectional view taken along line XI-XI of FIG. 1.

As shown in FIGS. 1 and 11, the antenna board section 20R6 is disk-shaped, has a diameter smaller than that of the transmission board section 20R5, and is attached on the other mounting surface side of the transmission board section 20R5 in parallel with the antenna board section 20R6. An antenna 43 is formed in the antenna board section 20R6 by placing a lead wire in a spiral shape. Both end portions (not shown) of the lead wire, which constitutes the antenna 43, are electrically connected to circuit portions of the transmission board section 20R5 respectively. Accordingly, the RF unit 42 can take out the signal having constant frequency, amplitude, and waveform from the signals to which the mixing is performed in the switch board section 20R3, and transmit the signal to the outside from the antenna board section 20R6.

Figure 2:
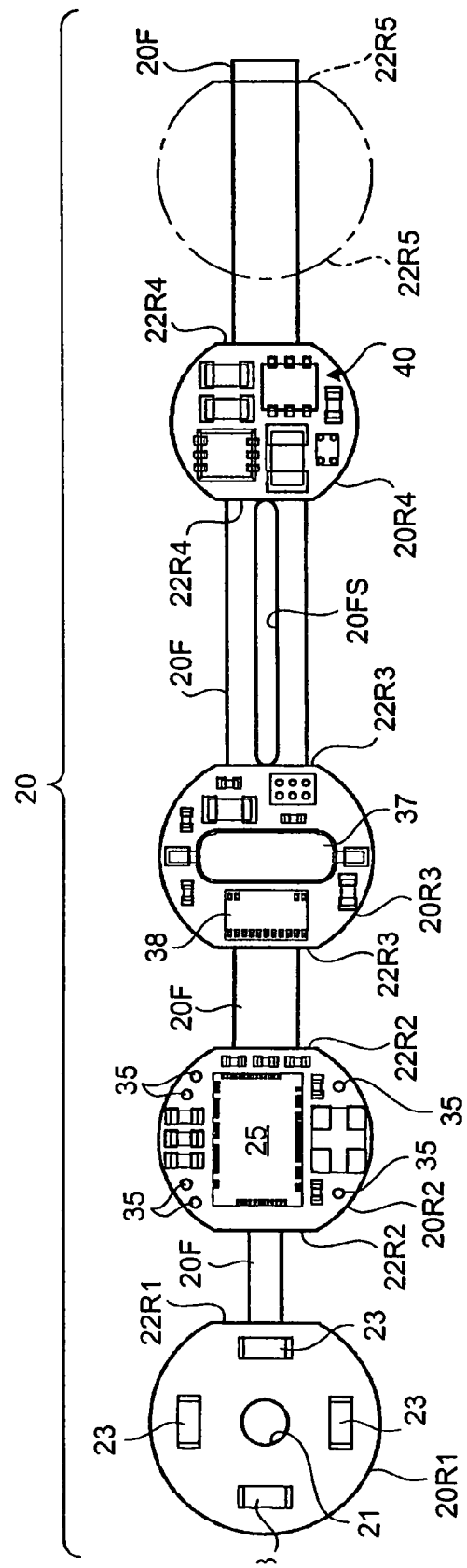
FIG. 2 is a development plan view showing a wiring board which is of an internal member of the capsule endoscope of FIG. 1.
Figure 3:
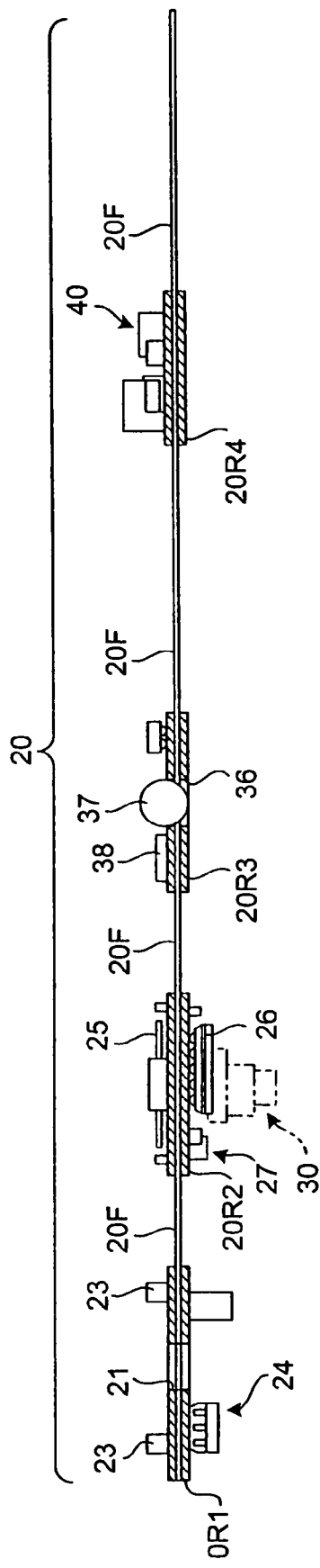
FIG. 3 is a sectional side view of FIG. 2.

As shown in FIGS. 2 to 4, the rigid wiring board sections 20R are previously formed by sequentially connecting the illumination board section 20R1, the imaging board section 20R2, the switch board section 20R3, the power source board section 20R4, and the transmission board section 20R5 in a straight line using the flexible wiring board section 20F. The illumination board section 20R1 to the power source board section 20R4 are integrally formed in a plate shape together with the flexible wiring board section 20F. After the electronic components are mounted on each of the illumination board section 20R1 to the power source board section 20R4, the linear rigid-flexible wiring board 20 is formed by connecting the transmission board section 20R5 integrated with the antenna board section 20R6 to the end portion of the flexible wiring board section 20F.

The electronic components can easily be mounted by an ordinary mounting technology to the rigid wiring board section 20R including the illumination board section 20R1 to the power source board section 20R4 which are integrally formed in the plate shape with the flexible wiring board section 20F. In a production stage at which the rigid wiring board section 20R and the flexible wiring board section 20F are integrally formed, the electrical connection is already established between the rigid wiring board section 20R and the flexible wiring board section 20F, so that shortening of the production process and facilitation of the assembling work can be achieved without the connection step.

The flexible wiring board sections 20F arranged between the rigid wiring board sections 20R have the different widths and lengths if needed. The relatively wide flexible wiring board section 20F arranged between the switch board section 20R3 and the power source board section 20R4 is divided into two pieces by a slit 20FS formed along the lengthwise direction.

First an operation confirming inspection of the functional circuit is performed to the linearly formed rigid-flexible wiring board 20. Then, as shown in FIG. 1, the flexible wiring board section 20F is appropriately folded while the adjacent rigid wiring board sections 20R oppositely face to each other, and the button cell 10 is sandwiched and held between the positive electrode contact member 39 of the switch board section 20R3 and the negative electrode contact member (not shown) of the power source board section 20R4 while the electrodes are fitted to the proper orientation, which allows the rigid-flexible wiring board 20 to be formed in a cylindrical block of an internal member which can be accommodated in the sealed container 100.

The operation confirming inspection is one which confirms whether the functional circuit is normally operated in the case where the electric power is supplied to the functional circuit. In the case of the rigid-flexible wiring board 20 having the above configuration, the operation confirming inspection of the functional circuit can be performed while the rigid-flexible wiring board 20 is formed in the straight line as shown in FIGS. 2 to 4. That is, in the rigid-flexible wiring board 20 in which the pad portion 35 is provided in the imaging board section 20R2, for example, the electric power can be supplied to the functional circuit by bringing a needle electrode of the external power source into contact with the pad portion 35 functioning as the external electric power terminal. Accordingly, even before the button cell 10, which is of the internal power source, is held between the positive electrode contact member 39 and the negative electrode contact member (not shown) like a production line of the rigid-flexible wiring board 20 and the like, the operation confirming inspection of the functional circuit can be performed to guarantee the secure operation.

When the operation confirming inspection is performed using the external power source, the button cell 10 which is of the internal power source is never consumed. Therefore, in the case where the relatively small button cell 10 is used, an operating time of the functional circuit can sufficiently be secured by the button cell 10. Further, if needed, not only can an initializing process be performed, but also the electric power is supplied from the external power source, such that the initial setting value of the functional circuit is input to the memory 38 of the switch board section 20R3 through the pad portion 35 which functions as the external input terminal.

Figure 16:
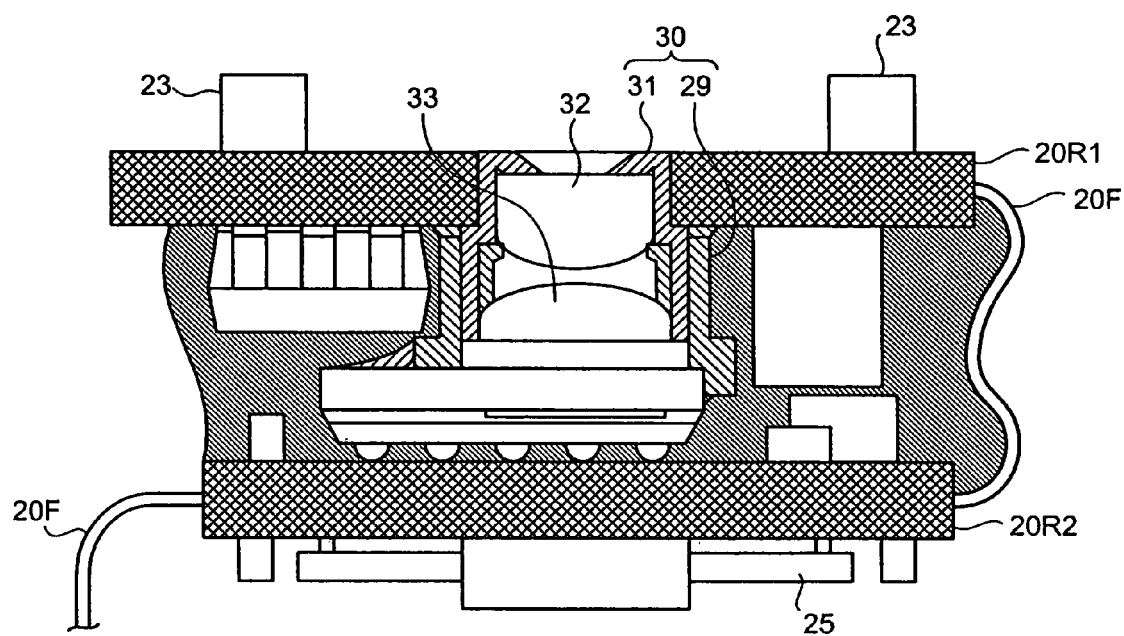
FIG. 16 is an enlarged cross-sectional view showing main parts of internal members applied to the capsule endoscope of FIG. 1.

In the case where the flexible wiring board section 20F is folded after the operation confirming inspection, as shown in FIGS. 1 and 16, the other mounting surface (back surface) of the illumination board section 20R1 and the other mounting surface (front surface) of the imaging board section 20R2 are caused to oppositely face to each other, the attachment portion 31b of the lens unit 30 is fitted in the attachment hole 21 of the illumination board section 20R1, and the rigid-flexible wiring board 20 is inserted until the shoulder portion 31d formed between the slide portion 31a and attachment portion of the lens frame 31 abuts on the other mounting surface of the illumination board section 20R1. The lens unit 30 fitted in the attachment hole 21 of the illumination board section 20R1 is positioned and held by the illumination board section 20R1, in the state where the step portion 31d formed between the slide portion 31a and attachment portion 31b of the lens frame 31 abuts on the other mounting surface of the illumination board section 20R1 while optical axes of the lens members 32 and 33 and the central axis of the visual field of the CCD 26 are aligned with the axial center of the illumination board section 20R1. Even in the state, when the cylindrical portion 29a of the holder 29 is slid with respect to the slide portion 31a of the lens frame 31, the distances of the imaging board section 20R2 and the CCD 26 are changed with respect to the lens members 32 and 33, which allows the focus of the CCD 26 to be adjusted. After the focus of the CCD 26 is adjusted, a gap between the illumination board section 20R1 and the imaging board section 20R2 is filled with an insulating sealing resin P, and the insulating sealing resin P is cured to hold the bonded state between the illumination board section 20R1 and the imaging board section 20R2.

At this point, after the CCD 26 and the holder 29 are assembled, the height to the step portion 31d from the front surface of the imaging board section 20R2, which is of the assembly height of the CCD 26 and the holder 29, is previously defined to be higher than the heights of various electronic components arranged in the front surface of the imaging board section 20R2.

The flexible wiring board section 20F is folded such that one of mounting surfaces of the imaging board section 20R2 oppositely faces one of mounting surfaces of the switch board section 20R3 while the other mounting surface of the switch board section 20R3 oppositely faces the other mounting surface of the power source board section 20R4. Therefore, the button cell 10 is sandwiched and held between the positive electrode contact member 39 and the negative electrode contact member (not shown).

After the button cell 10 is sandwiched and held between the switch board section 20R3 and the power source board section 20R4, a heat-shrinkable tube 44 is attached while surrounding the button cell 10, the switch board section 20R3, and the power source board section 20R4. Then, the button cell 10, the switch board section 20R3, and the power source board section 20R4 are pressure-bonded and held by properly heating the heat-shrinkable tube 44. Then, the gap between the imaging board section 20R2 and the switch board section 20R3 and the gap between the power source board section 20R4 and the transmission board section 20R5 are filled with the insulating sealing resin P and hardened, and the coupled state is held between the rigid wiring board sections 20R.

Figure 6:
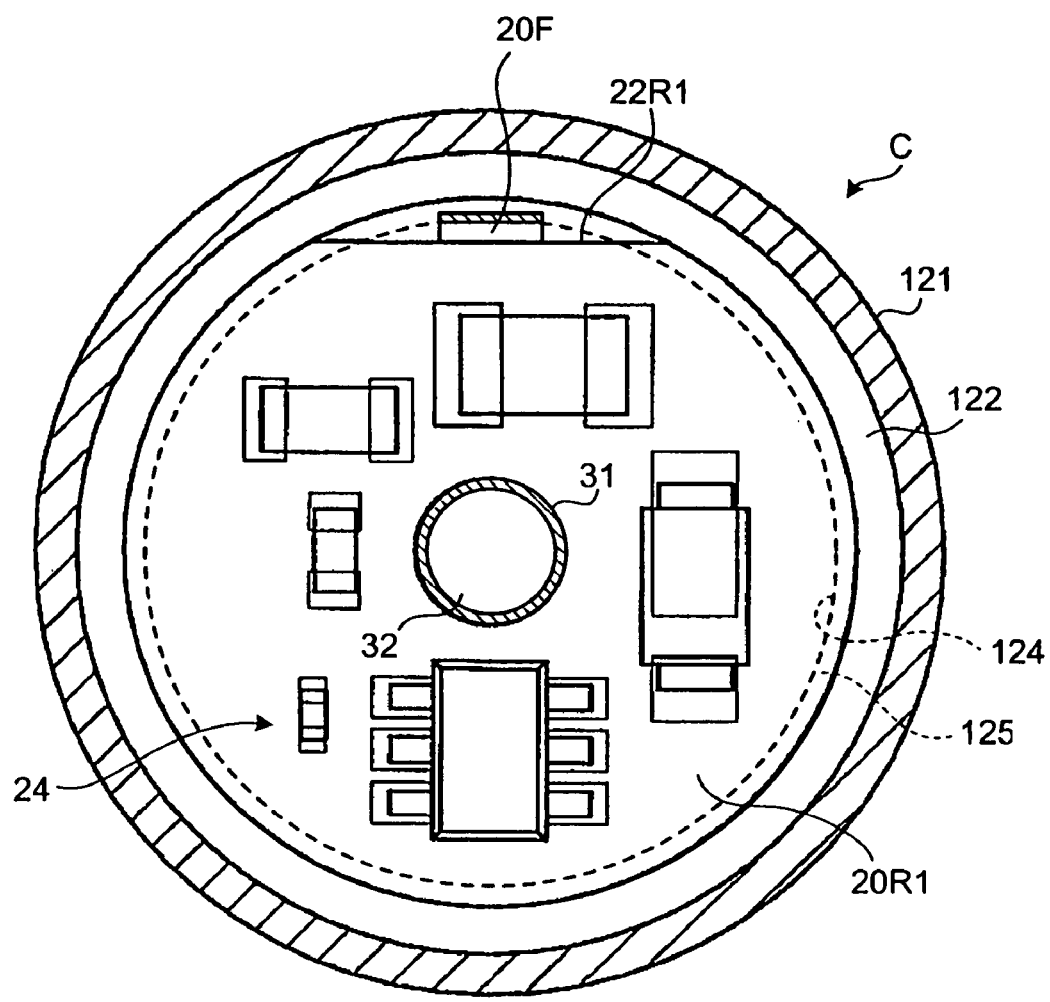
FIG. 6 is a cross-sectional view taken along line VI-VI of FIG. 1.
Figure 7:
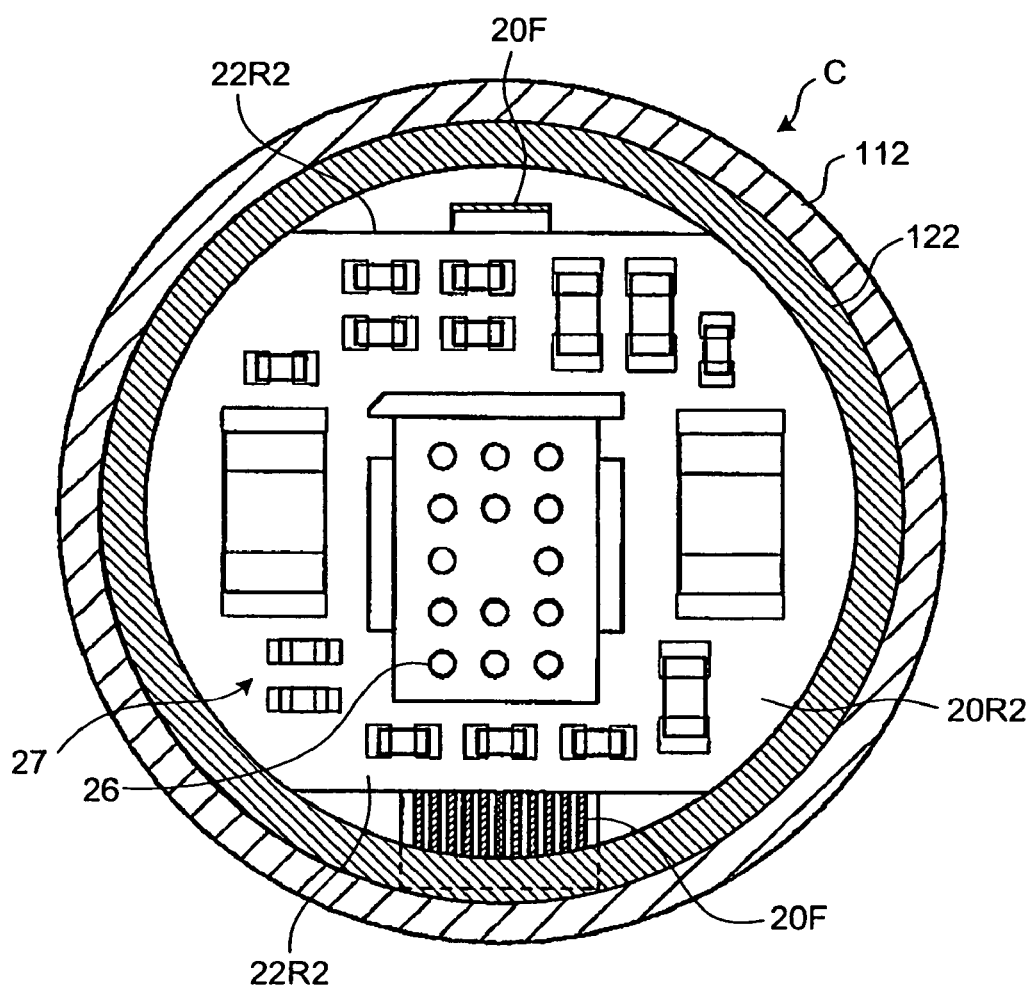
FIG. 7 is a cross-sectional view taken along line VII-VII in FIG. 1.

In the case where the cylindrical internal members are formed in the above manner, in the rigid-flexible wiring board 20, the flexible wiring board section 20F extends at a right angle from each straight-line portion 22R with respect to each disk-shaped rigid wiring board section 20R, so that each flexible wiring board section 20F can be folded easily and securely along each straight-line portion 22R from the region close to the rigid wiring board section 20R. Since the individual straight-line portion 22R is formed by cutting the disk-shaped rigid wiring board section 20R, for example, the folded flexible wiring board section 20F can be accommodated in the cut portion as shown in FIGS. 5 and 6. The flexible wiring board section 20F located in the outer circumferential portion of the button cell 10 is formed while divided into two pieces along the lengthwise direction by the slit 20FS, so that the flexible wiring board section 20F is brought into close contact with the button cell 10 while suiting the circumferential surface of the button cell 10. As a result, the large increase in outer-diameter size of each rigid wiring board section 20R or button cell 10 due to the flexible wiring board section 20F can be prevented.

On the other hand, the sealed container 100 which accommodates the button cell 10 and the rigid-flexible wiring board 20 is divided into a container main body 110 and a front cover 120.

Figure 17:
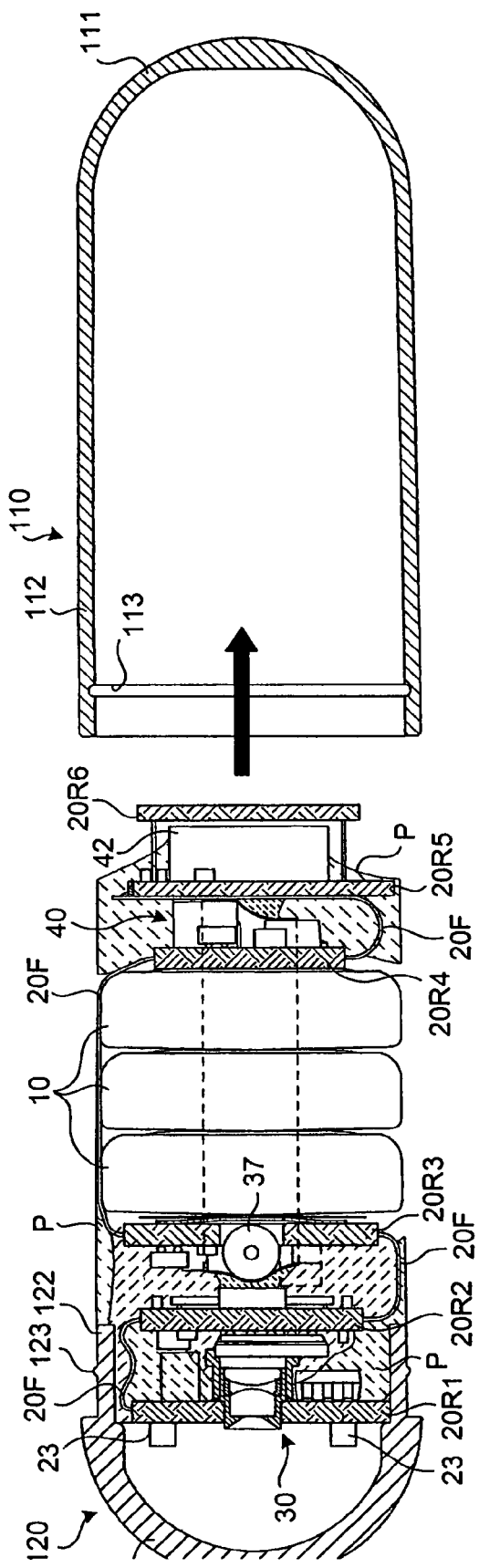
FIG. 17 is an exploded sectional side view showing a state where the internal members of the capsule endoscope of FIG. 1 are accommodated in a sealed container.

As shown in FIGS. 1 and 17, the container main body 110 includes a hemispherical and dome-shaped bottom portion 111 and a substantially cylindrical barrel portion 112. The barrel portion 112 extends continuously to the bottom portion 111. The bottom portion 111 and the barrel portion 112 are integrally molded by a synthetic resin material. For example, a cycloolefin polymer, polycarbonate, acryl, polysulfone, and urethane can be used as the synthetic resin material for molding the container main body 110. Particularly, polysulfone is preferably used in consideration of strength of the container main body 110.

The barrel portion 112 of the container main body 110 is tapered (not clearly shown in the drawings), and the diameter of the barrel portion 112 is slightly increased toward an opening side of the front. As shown in FIG. 1, not only is the size of the container main body 110 configured so that the rigid-flexible wiring board 20 and the button cell 10 can be accommodated, but also a gap with the accommodated internal members becomes the minimum, when the rigid-flexible wiring board 20 and the button cell 10 which are formed in a block as the internal member is inserted from the side of the antenna board section 20R6.

In the barrel portion 112 of the container main body 110, an engagement groove 113 is formed over the entire circumferences of the inner circumferential surface which is slightly shifted to the proximal end side of the opening of the front.

Figure 18:
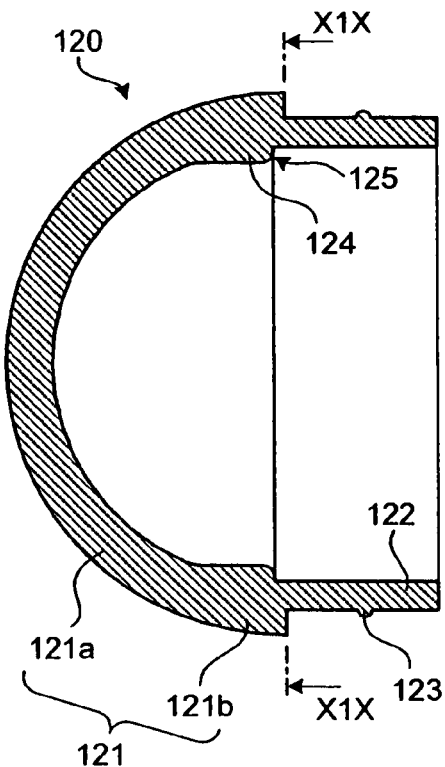
FIG. 18 is a sectional side view showing a front cover applied to the sealed container of the capsule endoscope of FIG. 1.
Figure 19:
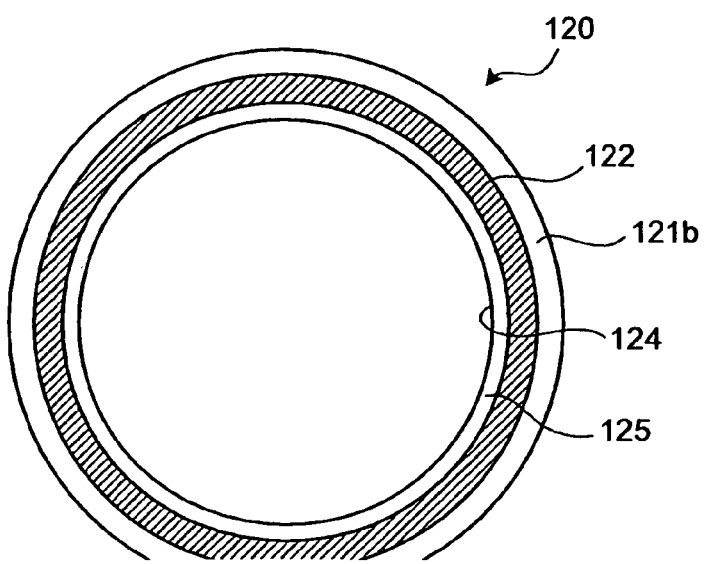
FIG. 19 is a cross-sectional view taken along line XIX-XIX in FIG. 18.

As shown in FIGS. 1, 18, and 19, the front surface side of the illumination board section 20R1 is covered with the front cover 120, and the front cover 120 includes a hemispherical and dome-shaped dome portion 121 and an engagement portion 122 that extends from the proximal end portion of the dome portion 121. The dome portion 121 and the engagement portion 122 are integrally molded by a synthetic resin material which becomes an optical material. Accordingly, the front cover 120 has transparency or translucency and transmits the image illuminated with the illumination light to the inside while transmitting the illumination light from the light-emitting device 23 to the outside. For example, a cycloolefin polymer, polycarbonate, acryl, polysulfone, and urethane can be used as the synthetic resin material for molding the front cover 120. Particularly, the cycloolefin polymer or polycarbonate is preferably used in consideration of optical performance and strength of the front cover 120.

In the front cover 120, the dome portion 121 has substantially the same outer-diameter as the front outer diameter of the barrel portion 112 in the container main body 110, and the engagement portion 122 has the outer diameter which can be fitted in the front inner circumference of the barrel portion 112 in the container main body 110. In the case where the front cover 120 is attached to the front portion of the container main body 110, the outer surface of the dome portion 121 can be fitted in the inner circumference of the front portion of the barrel portion 112 through the engagement portion 122 while being continuous to the outer surface of the barrel portion 112.

In the engagement portion 122 of the front cover 120, an engagement protrusion 123 is provided over the entire circumferences of the engagement portion 122 at the region corresponding to the engagement groove 113 of the container main body 110. The engagement protrusion 123 engages the engagement groove 113 of the container main body 110 to prevent unexpected drop-off of the front cover 120 from the container main body 110, in the case where the front cover 120 is attached to the front portion of the barrel portion 112. The inner circumferential diameter of the engagement portion 122 is formed so that the illumination board section 20R1 of the rigid-flexible wiring board 20 can be fitted in the inner circumference of the engagement portion 122.

In the front cover 120, a translucent portion 121a is set in a range (area surrounded by alternate long and two short dash lines in FIG. 1) which becomes a predetermined symmetrical area from a center of curvature of the dome portion 121, and a pupil portion 121b is provided over the entire circumferences of the region located on the outer circumferential surface of the translucent portion 121a.

The translucent portion 121a and the pupil portion 121b define the observation range of the image data with respect to the front cover 120. The translucent portion 121a of the front cover 120 is homogenously formed while having the even thickness. On the other hand, the pupil portion 121b is molded to have a thickness larger than that of the translucent portion 121a, and the pupil portion 121b constitutes a projection portion 124 which is projected inward from the inner circumferential surface of the engagement portion 122. In the projection portion 124, an abutting surface 125 located on the proximal end side extends in the direction orthogonal to the axial center of the front cover 120. In the case where the abutting surface 125 engagedly abuts on one of mounting surfaces of the illumination board section 20R1, the projection unit 124 is configured so that the optical axis of the lens unit 30 is aligned with the axial center of the front cover 120 while the center of the entrance pupil on the optical axis with respect to the lens unit 30 is aligned with the center of curvature (center of the entrance pupil in the front cover 120) of the front cover 120. In the projection portion 124, the inner diameter is set to be larger than the mounting area of the light-emitting device 23 in the illumination board section 20R1. In this configuration, in the case where the illumination board section 20R1 is rotated about the axial center, the projection portion 124 never interferes with the light-emitting device 23.

In the case where the sealed container 100 having the above configuration accommodates the rigid-flexible wiring board 20 and button cell 10 which are formed in the block, as shown in FIG. 17, after the illumination board section 20R1 is previously covered with the front cover 120, the insulating sealing resin P is applied to the circumferences of the rigid-flexible wiring board 20 and button cell 10 while the adhesive agent is applied to the inner circumferential surface of the container main body 110, and the internal member is inserted into the container main body 110 to engage the engagement protrusion 123 of the front cover 120 in the engagement groove 113 of the container main body 110. Therefore, the gap between the inner circumferential surface of the container main body 110 and the outer circumferential surfaces of the rigid and the gap between flexible wiring board 20 and button cell 10 are filled with the sealing resin P, and the adhesive intrudes between the engagement portion 122 of the front cover 120 and the inner circumferential surface of the container main body 110. In the state where the engagement protrusion 123 of the front cover 120 is engaged in the engagement groove 113 of the container main body 110, the adhesive agent located between the engagement protrusion 123 and the engagement groove 113 preferably spreads through the circumferential direction by relatively rotating the engagement protrusion 123 and the engagement groove 113.

In this case, as described above, when one of mounting surfaces of the illumination board section 20R1 is made only to abut on the abutting surface 125 of the front cover 120, the optical axis of the lens unit 30 is aligned with the axial center of the front cover 120 without inclining the optical axis of the lens unit 30 while the center of the entrance pupil with respect to the lens unit 30 is aligned with the center of curvature of the front cover 120. Additionally, in the case where the illumination board section 20R1 is inserted into the engagement portion 122, since the projection portion 124 of the front cover 120 never interferes with the light-emitting device 23 of the illumination board section 20R1, it is not necessary to consider an attitude about the axial centers of the projection portion 124 and light-emitting device 23. Accordingly, in the assembly, it is not necessary to adjust the position of the optical system with respect to the incident light, so that the assembling work can significantly easily be performed.

Figure 20:
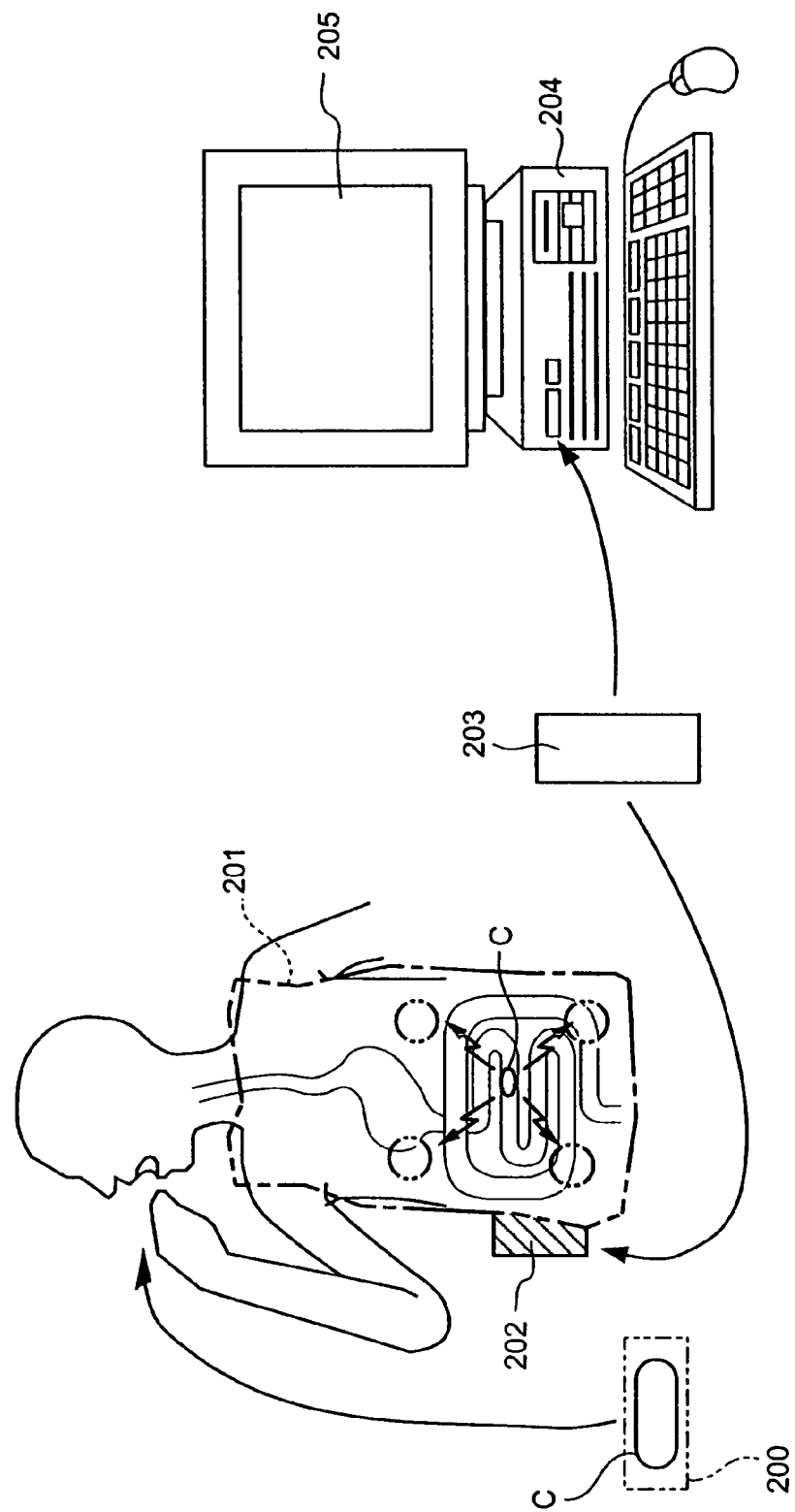
FIG. 20 is a conceptual view for explaining an example of use of the capsule endoscope.
Figure 21:
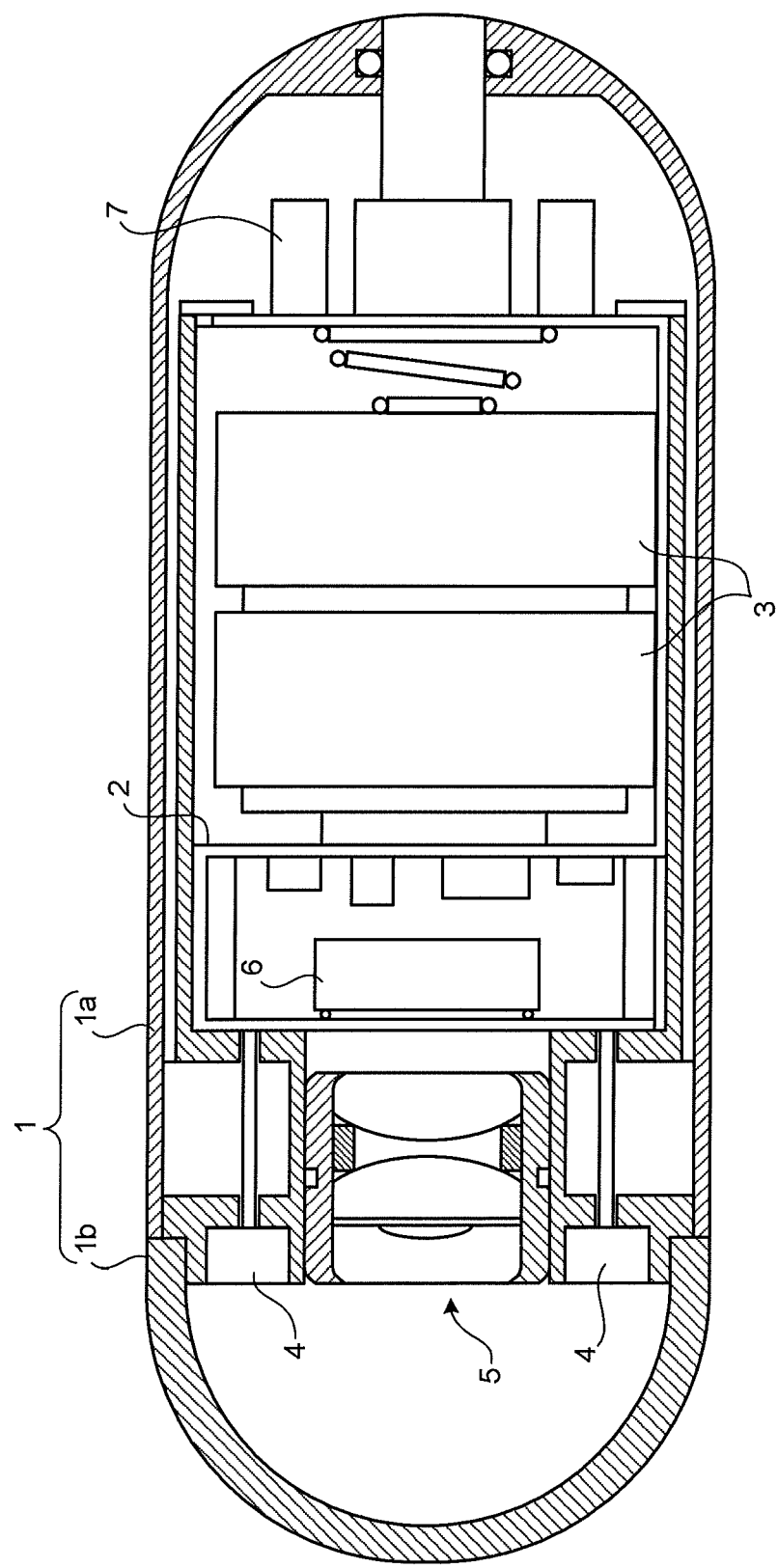
FIG. 21 is a sectional side view showing a conventional capsule endoscope.

The adhesive agent intruding between the inner circumferential surface of the container main body 110 and the outer circumferential surface of the engagement portion 122 in the front cover 120 secures the desired watertightness between the inner circumferential surface of the container main body 110 and the outer circumferential surface of the engagement portion 122, and there is no anxiety that a liquid such as a body fluid intrudes in the sealed container 100 in the case where the capsule endoscope C is putted into the body. Particularly, since the engagement protrusion 123 and the engagement groove 113 are engaged each other between the front cover 120 and the front portion of the container main body 110, the adhesive agent is never peeled off between the front cover 120 and the front portion of the container main body 110 even if the capsule endoscope C experiences a post-treatment process such as sterilizing process which is performed after the assembly, and there is no anxiety that the internal member is heated or short-circuited by the intrusion of the body fluid FIG. 20 is a conceptual view for explaining an example of the use of the capsule endoscope C. The operation of the capsule endoscope C will briefly be described with reference to FIG. 20.

The capsule endoscope C of the embodiment is taken out from a package 200 into which the permanent magnet (not shown) is incorporated, the reed switch 37 is started to continuously turn on the electric power supply with respect to the functional circuit through the DC-DC converter 40 from the button cell 10 which is of the internal power source.

In this state of things, when the subject wearing a jacket 201 swallows the capsule endoscope C, each unit of the functional circuit can be driven to obtain the image data of the subject by an instruction from the DSP 25 until the capsule endoscope C is discharged to the outside of the body. More specifically, the observation range of the subject such as gaster, small intestine, and the large intestine is illuminated with the illumination light emitted from the translucent portion 121a through the translucent portion 121a of the front cover 120, the reflected light incident through the translucent portion 121a of the front cover 120 is focused to the CCD 26 through the lens unit 30, and the reflected light focused to the CCD 26 is output as the image signal.

The image signal output from the CCD 26 is modulated and amplified by the RF unit 42, the image signal is wirelessly transmitted to the outside through the antenna 43, and the image data is sequentially stored in an external storage device 203 such as a CompactFlash® memory in a receiver 202 attached to the jacket 201 in the form of the image data. For example, the image data stored in the external storage device 203 is visualized on a display 205 through a computer 204, and the image data becomes a target of a diagnosis by a doctor or a nurse.

During the operations, in the capsule endoscope C, not only is the optical axis of the lens unit 30 aligned with the axial center of the front cover 120, but also the center of the entrance pupil with respect to the lens unit 30 is aligned with the center of curvature of the front cover 120. Therefore, all the incident light beams incident from the translucent portion 121*a* provided in the dome unit 121 of the front cover 120 are focused onto the pixel surface of the CCD 26 by the lens members 32 and 33 of the lens unit 30, and the significantly favorable image data can be obtained because the homogeneous translucent portion 121*a* is formed in the even thickness.

The positioning of the optical system with respect to the incident light is correctly performed without any adjustment work by causing one of mounting surfaces of the illumination board section 20R1 to abut on the abutting surface 125 of the front cover 120. Therefore, there is no anxiety that the assembling work becomes complicated.

Since the light-shielding portion 31*c* is provided in the lens frame 31 which holds the lens members 32 and 33, in the dome portion 121 of the front cover 120, the incident light passing through the pupil portion 121*b* located on the outer circumference side of the translucent portion 121*a* can securely be blocked to effectively prevent the generation of flare in the image data.

In the capsule endoscope C, the abutting portion 29*c* is brought into close contact with the cover glass 28, extends from the lower edge portion of the holder 29 which holds the lens frame 31 supporting the lens members 32 and 33 focusing the image to CCD 26, and abuts on the outline of the cover glass 28. Therefore, the lens frame 31 is positioned at a predetermined position with respect to the CCD 26, so that the lens frame 31 can easily be positioned for a short period of time at a predetermined position with respect to a light acceptance surface of the CCD 26.

The exposed surface of the cover glass 28 is shielded by the black-colored adhesive agent while the holder 29 is fixed to the cover glass 28 with the black-colored adhesive agent, so that the assembling work can be performed with the simple configuration, and the clear image can be obtained in the CCD 26.

It is not necessary that the illumination board section 20R1 and the imaging board section 20R2 be separately connected by the lead wire or the like, and can simply be assembled as compared with the conventional art.

In the embodiment, since the illumination board section 20R1 and the abutting surface 125 of the projection portion 124 provided in the front cover 120 abut on each other while being relatively rotatable, it is not necessary to consider the attitude about the axial centers of the illumination board section 20R1 and the abutting surface 125, and the assembling work can be easily performed. However, it is not always necessary that the illumination board section 20R1 and the abutting surface 125 of the front cover 120 abut on each other while being relatively rotatable. It is not always necessary that the projection portion 124 of the front cover 120 be formed over the entire circumferences, but it is sufficient to cause the projection unit 124 to abut on one of mounting surface of the illumination board section 20R1 at least three points.

In the rigid-flexible wiring board 20, the illumination board section 20R1, the imaging board section 20R2, the switch board section 20R3, and the power source board section 20R4 are sequentially formed in this order in the straight line by the flexible wiring board section 20F. However, the illumination board section 20R1, the imaging board section 20R2, the switch board section 20R3, and the power source board section 20R4 may sequentially be located when the flexible wiring board section 20F is folded. For example, when the illumination board section 20R1, the imaging board section 20R2, the switch board section 20R3, and the power source board section 20R4 are located in the same plane, the illumination board section 20R1, the imaging board section 20R2, the switch board section 20R3, and the power source board section 20R4 may not always be formed in the straight line.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic imaging apparatus, comprising:
   an image sensor having a polygonal outline;
   a lens for focusing an image onto the image sensor;
   a lens support member abutting on the image sensor, and supporting the lens; and
   an abutting portion formed to extend from a lower edge portion of the lens support member, the abutting portion being abuttable on at least two adjacent sides on a side surface of an outline of the image sensor, wherein
   the lens support member is positioned by abutting the abutting portion on the at least two adjacent sides so that the lens is positioned at a predetermined position of the image sensor, wherein the lens support member further has a reinforcement portion having substantially a same shape as the abutting portion, the reinforcement portion not abutting the side surface.

2. The endoscopic imaging apparatus according to claim 1, wherein the lens support member is fixed to the image sensor with a black-colored adhesive agent, and an exposed surface of the image sensor is shielded with the adhesive agent.

3. The endoscopic imaging apparatus according to claim 1, wherein:
   the image sensor has a solid-state imaging device and a cover glass that is layered on a top surface of the image sensor, and
   the lens support member is attached to the cover glass, and is positioned with respect to the image sensor through the cover glass.

4. The endoscopic imaging apparatus according to claim 3, wherein the lens support member includes:
   a lens frame which supports the lens; and
   a holder which holds the lens frame;
   the holder having a base attached to the cover glass, a cylindrical portion extending upwards from the base, and the abutting portion extending in a direction opposite from a direction to which the cylindrical portion extends; and
   the lens frame is slidably fitted in an inner circumference surface of the cylindrical portion of the holder.

5. The endoscopic imaging apparatus according to claim 4, wherein the lens support member is fixed to the image sensor with a black-colored adhesive agent, and an exposed surface of the image sensor is shielded with the adhesive agent.

6. The endoscopic imaging apparatus according to claim 3, wherein the lens support member is fixed to the image sensor with a black-colored adhesive agent, and an exposed surface of the image sensor is shielded with the adhesive agent.

7. A method for manufacturing an endoscopic imaging apparatus, comprising:

positioning a holder that supports a lens frame by abutting an abutting portion that extends from the holder on two adjacent sides on a side surface of an outline of an image sensor;

fixing the holder positioned by the positioning to the image sensor; and fitting the lens frame in the holder so that the lens frame slides with respect to the holder to adjust a focus position, wherein the holder further has a reinforcement portion having substantially a same shape as the abutting portion, the reinforcement portion not abutting the side surface.

* * * * *